United States Patent [19]
Murray et al.

[11] Patent Number: 4,748,270
[45] Date of Patent: May 31, 1988

[54] PREPARATION OF AROMATIC CYANATES

[75] Inventors: Daniel J. Murray, Saginaw; Edmund P. Woo, Midland, both of Mich.

[73] Assignee: The Dow Chemical Company, Midland, Mich.

[21] Appl. No.: 552,515

[22] Filed: Nov. 16, 1983

[51] Int. Cl.$^4$ ............................................. C07C 69/00
[52] U.S. Cl. ..................................................... 560/301
[58] Field of Search ................ 260/453 AR, 453 AM, 260/453 P; 560/301

[56] References Cited

U.S. PATENT DOCUMENTS

| | | |
|---|---|---|
| 3,107,261 | 10/1963 | Gerber et al. . |
| 3,383,359 | 5/1968 | Weitzel et al. . |
| 3,448,079 | 6/1969 | Grigat et al. . |
| 3,553,244 | 1/1971 | Grigat et al. . |
| 3,740,348 | 6/1973 | Grigat et al. . |
| 3,755,402 | 8/1973 | Grigat et al. . |
| 3,763,206 | 10/1973 | Brunetti ...................... 260/453 AR |
| 3,978,028 | 8/1976 | Sundermann et al. . |
| 3,994,949 | 11/1976 | Meyer et al. . |
| 4,049,630 | 9/1977 | Sundermann et al. . |
| 4,060,541 | 11/1977 | Sundermann ............... 260/453 AM |
| 4,097,455 | 6/1978 | Burkhardt et al. . |

OTHER PUBLICATIONS

Martin et al, Organic Synthesis, 61, pp. 35–38.
Coleman et al, Inorganic Synthesis, 2, 90–94 (1946).

*Primary Examiner*—Alan Siegel
*Attorney, Agent, or Firm*—Norman L. Sims

[57] ABSTRACT

A process for the preparation of an aromatic cyanate which comprises (a) preparing in situ a cyanogen chloride by contacting a solution of chlorine in a chlorinated hydrocarbon with an aqueous solution of an alkali metal cyanide at a temperature of 0° C. or below under conditions such that a cyanogen chloride is prepared; (b) physically separating the chlorinated hydrocarbon in which the cyanogen chloride is dissolved from the aqueous layer in which an alkali metal chloride salt is dissolved; and (c) contacting the cyanogen chloride dissolved in the chlorinated hydrocarbon with a hydroxy-substituted aromatic compound dissolved in a chlorinated hydrocarbon, a secondary alcohol or a tertiary alcohol, in the presence of a tertiary amine at a temperature of about 0° C. or less under conditions such that a polyaromatic cyanate is prepared.

9 Claims, No Drawings

PREPARATION OF AROMATIC CYANATES

BACKGROUND OF THE INVENTION

This invention relates to a process for the preparation of aromatic cyanates. More specifically, it relates to the preparation of aromatic cyanates using cyanogen chloride generated in situ.

Aromatic cyanates are useful in the preparation of polytriazines. Polytriazines are useful as cure in place resins and can be fabricated in the form of shaped articles, where thermostability, chemical inertness, and solvent resistance is desirable or required.

There are several known methods for the preparation of cyanogen chloride using high temperature vapor phase reactions of chlorine, hydrogen cyanide, or oxygen, hydrogen chloride and hydrogen cyanide, but the product prepared has to be carefully separated from unreacted starting materials using complicated purification procedures. It is known to prepare cyanogen chloride by bubbling chlorine gas into a mixture of zinc sulfate and potassium cyanide in an aqueous medium. See *Handbook of Preparative Inorganic Chemistry*, 1, 662 (1963), Academic Press, N.Y. The presence of zinc sulfate rules out the possibility of using this crude solution for polycyanate synthesis as it is known that zinc salts are effective catalysts for the cyclotrimerization of aryl cyanates. It is further known to prepare cyanogen chloride by adding chlorine gas to a slurry of solid sodium cyanide in carbon tetrachloride and acidic acid. Aryl cyanates are very reactive towards nucleophiles such as carboxylic acids, therefore, this procedure is not suitable when the cyanogen chloride is to be used in situ to further prepare aryl cyanates. See *Inorganic Synthesis*, 2, 90 (1946).

Martin et al., *Organic Synthesis*, 61, 35, disclose a process which involves the addition of an aqueous solution of sodium cyanide to a mixture of bromine and water to prepare cyanogen bromide and sodium chloride. A solution of a phenolic compound in carbon tetrachloride is then added followed by triethylamine. The removal of the solvent from the organic layer and distillation of the residue gives aryl cyanate.

What is needed is a process for the in situ preparation of cyanogen chloride wherein the cyanogen chloride can thereafter be used to prepare stable aromatic cyanates.

SUMMARY OF INVENTION

The invention is a process for the preparation of an aromatic cyanate which comprises (a) preparing in situ a cyanogen chloride by contacting a solution of chlorine in a chlorinated hydrocarbon with an aqueous solution of an alkali metal cyanide at a temperature of 0° C. or below under conditions such that a cyanogen chloride is prepared; (b) physically separating the chlorinated hydrocarbon in which the cyanogen chloride is dissolved from the aqueous layer in which an alkali metal chloride salt is dissolved; and (c) contacting the cyanogen chloride dissolved in the chlorinated hydrocarbon with a hydroxy-substituted compound dissolved in a chlorinated hydrocarbon, a secondary alcohol or a tertiary alcohol, in the presence of a tertiary amine at a temperature of about 0° C. or less under conditions such that a polyaromatic cyanate is prepared.

This process results in the preparation of stable aromatic cyanates. Furthermore, the aromatic cyanates so prepared are easily recoverable in a useable form. This process further allows the preparation of cyanogen chloride in a manner such that the cyanogen chloride can thereafter be used directly to prepare aromatic cyanates.

DETAILED DESCRIPTION

The process of this invention can be used to prepare any aromatic cyanate compound, wherein there is a cyanate group attached to an aromatic radical. Preferred aromatic cyanate compounds include those which correspond to the formula:

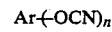

wherein Ar represents an aromatic radical, and n is an integer of between 1 and 5.

More preferable aromatic cyanates correspond to the formula:

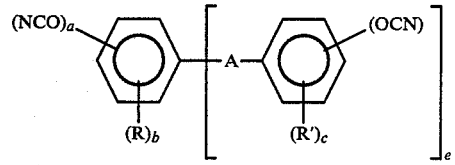

wherein each R is the same or different and represents hydrogen, halogen, straight and branched $C_1$-$C_{20}$ alkyl, phenyl, alkoxy radicals having from 1 to 4 carbon atoms, alkoxy carbonyl radicals having from 1 to 4 carbon atoms in the alkyl group or two adjacent radicals R on the same nucleus may together form a carbocyclic 5- or 6-membered ring, two adjacent radicals R may, together with a hetero atom (O, S, N), form a 5- or 6-membered heterocyclic ring; R' has the same meaning as R or represents the group:

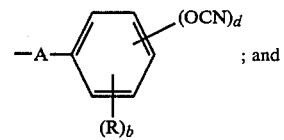

; and

A represents a direct bond, a $C_1$-$C_{20}$ alkylene group optionally substituted by $C_1$-$C_4$ alkyl or phenyl, a cycloaliphatic or aromatic 5- or 6-membered ring optionally interrupted by oxygen, a sulfonyl group (—$SO_2$—), a carbonyl dioxide group

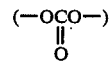

or a carbonyl group; a represents a number of from 1 to 5 when e≧1, and a number of from 2 to 5 when e=0; b represents 5-a when e≧1 and 6-(a+d) when e=0; c represents 5-d; d represents a number of from 0 to 5; and e represents 0, 1, 2 or 3, with a proviso that the sum of a and d is always a number from 2 to 5.

Included in aromatic cyanates prepared by this invention are 1,3- and 1,4-dicyanatobenzene, 2-tert-butyl-1,4-dicyanatobenzene, 2,4-dimethyl-1,3-dicyanatobenzene, 2,5-di-tert-butyl-1,4-dicyanatobenzene, tetramethyl-1,4-dicyanatobenzene, 2,4,6-trimethyl-1,3-dicyanatobenzene, 4-chloro-1,3-dicyanatobenzene, 1,3-, 1,4-, 1,5-, 1,6-, 1,7-, 1,8-, 2,6- or 2,7-dicyanatonaphthalene, 1,3,5-tricyanatobenzene; 4,4'-dicyanatodiphenyl, 2,2'-dicyantodiphenyl, 3,3', 5,5'-tetramethyl-4,4'-dicyanatodiphenyl, 3,3', 5,5'-tetrachloro-4,4'-dicyanatodiphenyl, 3,3', 5,5'- tetrachloro-2,2'-dicyanatodiphenyl, 2,2',6,6'-tetracloro-4,4'-dicyanatodiphenyl, 4,4'-bis[(3-cyanato)-phenoxy]-diphenyl, 4,4'-bis-[(4-cyanato)-phenoxy]-diphenyl; 2,2'-dicyanato-1,1'-binaphthyl; 4,4'-dicyanatodiphenyl ether, 3,3', 5,5'-tetramethyl-4,4'-dicyanatodiphenyl ether, 3,3', 5,5'-tetrachloro-4,4'-dicyanatodiphenyl ether, 4,4'-bis-[p-cyanatophenoxy]-diphenyl ether, 4,4'-bis-[p-cyanatophenylisopropyl]-diphenyl ether, 4,4'-bis-[p-cyanatophenoxy]-benzene, 4,4'-bis-[m-cyanatophenoxy]-diphenyl ether, 4,4'-bis-[4-(4-cyanatophenoxy)-phenyl sulfone]-diphenyl ether; 4,4'-dicyanatodiphenyl sulfone, 3,3',5,5'-tetramethyl-4,4'-dicyanatodiphenyl sulfone, 3,3',5,5'-tetrachloro-4,4'-dicyanatodiphenyl sulfone, 4,4'-bis-[p-cyanatophenylisopropyl]-diphenyl sulfone, 4,4'-bis-[(4-cyanato)-phenoxy]-diphenyl sulfone, 4,4'-bis-[(3-cyanato)-phenoxy]-diphenyl sulfone, 4,4'-bis-[4-(4-cyanatophenylisopropyl)-phenoxy]-diphenyl sulfone, 4,4'-bis-4-cyanatophenyl sulfone)-phenoxy]-diphenyl sulfone, 4,4'-bis-[4-(4-cyanato)-diphenoxy]-diphenyl sulfone, 4,4'-dicyanatodiphenyl methane, 4,4'-bis-[p-cyanatophenyl]-diphenyl methane, 2,2-bis-(p-cyanatophenyl)-propane, 2,2-bis-(3,5-dimethyl-4-cyanatophenyl)-propane, 2,2-bis-(3,5-dichloro-4-cyanatophenyl)-propane, 1,1-bis-[p-cyanatophenyl]-cyclohexane, bis-[2-cyanato-1-naphthyl]-methane, 1,2-bis-[p-cyanatophenyl]-1,1,2,2-tetramethyl ethane, 4,4'-dicyanatobenzophenone, 4,4'-bis-(4-cyanato)-phenoxybenzophenone, 1,4-bis-[p-cyanatophenylisopropyl]-benzene, 2,2', 5,5'-tetracyanatodiphenyl sulfone; polycyanic acid esters of novolaks (reaction products of phenol or alkyl- or halogen-substituted phenols with formaldehyde in acid solution) having from 3 to 5 OCN groups and the like.

The aromatic cyanates are prepared by reacting a suitable aromatic compound with cyanogen chloride. Any hydroxy-substituted compound which contains an aromatic radical which is substituted with a hydroxy group and which will react with cyanogen chloride to prepare an aromatic cyanate is useful in this reaction. Preferred hydroxy-substituted aromatic compounds include those which correspond to the formula:

wherein Ar and n are as defined hereinbefore. More preferred hydroxy-substituted aromatic compounds include those which correspond to the formula:

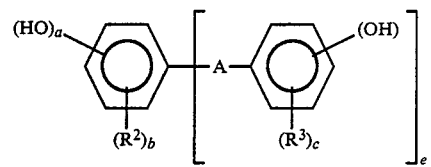

wherein each $R^2$ is the same or different and represents hydrogen, halogen, straight and branched $C_1$–$C_{20}$ alkyl, phenyl, alkoxy radicals having from 1 to 4 carbon atoms, alkoxy carbonyl radicals having from 1 to 4 carbon atoms in the alkyl group or two adjacent radicals $R^2$ on the same nucleus may together form a carbocyclic 5- or 6-membered ring, two adjacent radicals $R^2$ may, together with a hetero atom (O, S, N), form a 5- or 6-membered heterocyclic ring; $R^3$ has the same meaning as $R^2$ or represents the group:

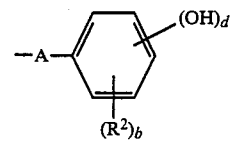

wherein a, b, c, d, e, are as defined hereinbefore. Examples of hydroxy-substituted aromatic compounds useful in this invention include phenol, dihydroxybenzenes, trihydroxybenzenes, naphthol, binaphthol, bisphenol A, and compounds which correspond to the formula:

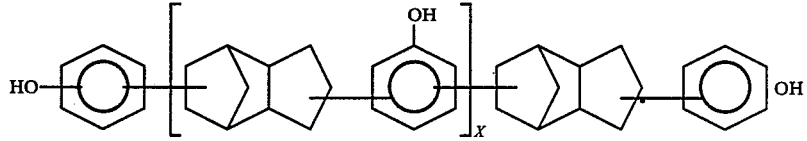

wherein x is a real number of between zero and 5, inclusive.

In the formulas described hereinbefore, Ar is preferably a benzene, naphthalene, phenanthracene, anthracene, or biaryl radical, or 2 or more aromatic radicals bridged by alkylene moieties. Ar is more preferably benzene, naphthalene, biphenyl, binaphthol, or a diphenyl alkylene.

Generally, the process of this invention involves the in situ preparation of cyanogen chloride, and thereafter the use of the cyanogen chloride to prepare an aromatic cyanate from a hydroxy aromatic compound. The alkali metal cyanide and chlorine can be contacted in any mole ratio which results in the preparation of cyanogen chloride. It is preferable to contact the alkali metal cyanide and chlorine in a mole ratio of between about 1.15:1 and 1.0:1.0. The mole ratio is more preferably between about 1.05:1.00 and 1.00:1.00. It is most preferable to run the reaction with a stoichiometric ratio of chlorine to alkali metal cyanide. When excess chlorine is used, the residual chlorine will react with the phenol in later processing. Furthermore, if excess alkali metal cyanide is used, its presence results in lower product purity of the aromatic cyanates prepared. In the preparation of a cyanogen chloride an aqueous solution of an alkali metal cyanide is contacted with a solution of chlorine in a suitable organic solvent. Organic solvents useful for dissolving the chlorine include chlorinated hydrocarbons, for example, aromatic chlorinated hydrocarbons and aliphatic chlorinated hydrocarbons. Preferable solvents include aliphatic chlorinated hydrocarbons. The concentration of chlorine in the chlorinated hydrocarbon solvent is preferably between about 0.5 and 3.0 molar, and most preferably between about 1 and 2 molar. The concentration of alkali metal cyanide in the aqueous solution is preferably between 10 percent by weight and completely saturated, it is most preferable to use an aqueous solution saturated with the alkali metal cyanide.

Alkali metal refers herein to sodium, potassium, lithium, rubidium, and cesium. Preferred alkali metals are sodium, potassium and lithium, with sodium being most preferred.

The preparation of cyanogen chloride can take place at any temperature at which the cyanogen chloride is formed. It is preferable to run this reaction at a temperature of $-10°$ C. or below. It is most preferable to run the process at a temperature of $-15°$ C. or below. At temperatures above $-10°$ C., the cyanide-containing compounds undergo trimerization. At temperatures below $-15°$ C., optimum results are achieved.

This process can be done in the presence of air, but it is preferable to run the reaction under an inert gas atmosphere. The pressure used during the reaction can be atmospheric or superatmospheric pressure.

After contacting the chlorine in chlorinated hydrocarbon solution with the aqueous alkali metal cyanide solution, the reaction mixture separates into two phases, one phase is an organic layer which contains the cyanogen chloride product. The second layer is an aqueous layer containing an alkali metal chloride.

In the second step of this process, step B, the organic layer containing the cyanogen chloride is separated from the aqueous layer containing the alkali metal chloride. This separation is important in the preparation of pure aromatic cyanates, as the presence of the aqueous layer creates significant problems in the preparation of pure and stable aromatic cyanates. It is possible to have up to 10 percent water present during later processing, but it is most preferable to have less than 1 percent by weight of water present.

In the third step, step C, the organic layer containing the cyanogen chloride is contacted with a mixture of a hydroxy-substituted aromatic compound in a suitable solvent. Examples of suitable solvents include secondary alcohols, tertiary alcohols, or chlorinated hydrocarbons. Preferred solvents are tertiary alcohols or aliphatic chlorinated hydrocarbons, with isopropyl alcohol and methylene chloride being most preferred.

The cyanogen chloride and hydroxy-substituted aromatic compounds are contacted in a mole ratio of between about 1.0:1 and 2.0:1.0. The cyanogen chloride to hydroxy-substituted aromatic compound mole ratio is preferably between about 1.1:1 and 2:1.

This contacting is done in the presence of dilute base. At least a stoichiometric ratio of base to cyanogen chloride is used. It is preferable to use an excess of 1 to 5 mole percent of base over cyanogen chloride, with an excess of 1 to 2 mole percent being preferred. Examples of base which can be used include alkali or alkaline metal hydroxides, alkali or alkaline metal carbonates, alkali or alkaline metal bicarbonates, or tertiary amines. Preferred bases are the tertiary amines, with the aliphatic tertiary amines being most preferred.

This step can be run at any temperature at which the preparation of an aromatic cyanate from a hydroxy substituted aromatic compound takes place. Preferable temperatures are below about 0° C., with temperatures less than about $-15°$ C. being most preferred.

This process may be run in the presence of air, but it is preferable to run the process under an inert gas atmosphere. The process may be run at any pressure at which the reaction proceeds. Atmospheric and superatmospheric pressures are preferred.

The aromatic cyanates prepared by the process of this invention can be recovered in the following manner. The reaction solution is washed with a dilute base solution so as to remove any excess cyanogen chloride present. A sufficient amount of dilute base to react with the excess cyanogen chloride present is used. Generally, the concentration of base in the aqueous solution is between 1 and 20 percent by weight, with 5 to 10 percent by weight being preferred.

Thereafter, the reaction solution is washed with water so as to remove any salt prepared from the hydrochloride and base. Generally, about one-half of the volume of the reaction mixture of water is useful.

The reaction solution can then be contacted with dilute acid to neutralize any base which may be present. Generally, a sufficient amount of dilute acid to remove any base may be used. This step is only necessary if the base used in step C was a tertiary amine. Acids useful in this process include hydrochloric acid, sulfuric acid, and phosphoric acid. Any dilute solution of acid in water is suitable, the concentration of acid in water is preferably between about 1 and 20 percent by weight, with 5 to 10 percent by weight being most preferred.

Thereafter, the reaction solution can be contacted with water again so as to remove any other impurities which may be present. Generally, an amount of water which is about half of the volume of the reaction solution is suitable.

To recover the aromatic cyanate, the reaction solution can thereafter be dried through the use of a desiccant. This drying can be done by processes well-known in the art. After drying, the organic solvent can be removed by evaporation or other means well-known in the art so as to leave the aromatic cyanate product.

SPECIFIC EMBODIMENTS

The following examples are included for illustrative purposes only, and are not intended to limit the scope of the invention or claims.

EXAMPLE 1

Chlorine (0.5 mole, 35.5 grams) is introduced into 500 ml of dichloromethane previously cooled to about $-10°$ C. To this solution is added a solution of sodium cyanide (0.5 mole, 24.5 grams) in 100 ml of water while maintaining the temperature of solution at about $-10°$ C. After the addition is complete, both the organic and the aqueous layers are colorless indicating the absence of unreacted chlorine. The organic layer is transferred to another reactor, with care being taken to exclude the aqueous layer. To this solution is added bisphenol A (0.175 mole, 39.9 g) in isopropyl alcohol (100 ml) and triethylamine (0.385 mole, 38.88 g). After the addition is complete, the reaction mixture is stirred for 5 minutes and then washed with a saturated sodium bicarbonate solution, water, dilute hydrochloric acid, and then water. The dichloromethane solution is dried over anhydrous sodium sulfate. Upon removal of the drying agent and the solvent, a crystalline material results which is isolated by filtration and washed with a small amount of cold methanol. The product recovered is bisphenol A dicyanate, the yield is 84.6 percent.

A portion of the bisphenol A dicyanate is placed on a gel plate at a temperature of 177° C., and the gel time is measured. Gel time is defined as the elapsed time for the transformation of the sample from a liquid to a solid when it is placed on a heated surface. The gel time of the bisphenol A dicyanate is 6.5 hours.

EXAMPLE 2

Chlorine (0.5 mole, 35.5 g) is introduced into 500 ml of dichloromethane, which has been previously cooled to about −10° C. To this solution is added a solution of sodium cyanide (0.5 mole, 24.5 g) in 80 ml of water while maintaining the temperature of the solution at about −10° C. After the addition is complete, the organic layer is transferred to another reactor, with care being taken to exclude the aqueous layer. To this solution is added a solution of bisphenol A (0.2 mole) in isopropyl alcohol (100 ml) along with triethylamine (0.44 mole). After the addition is complete, the reaction mixture is stirred for 5 minutes and is then washed with a saturated sodium bicarbonate solution, water, dilute hydrochloric acid, and then water. The dichloromethane solution is dried over anhydrous sodium sulfate. Upon removal of the drying agent and the solvent, a crystalline material results which is isolated by filtration and washed with a small amount of cold methanol. The product is bisphenol A dicyanate recovered in an 89.6 percent yield. The gel time of the product recovered is measured at greater than 7 hours.

EXAMPLE 3

Chlorine (1.0 mole, 71 g) is introduced into 600 ml of dichloromethane previously cooled to about −10° C. To this solution is added a solution of sodium cyanide (1.0 mole, 49 g) in 150 ml of water while maintaining the temperature of the solution at about −10° C. After the addition, the organic layer is transferred to another reactor, with care being taken to exclude the aqueous layer. To the organic layer is added bisphenol A (0.4 mole) dissolved in isopropyl alcohol (200 ml) and triethylamine (0.88 mole). After the addition is complete, the reaction mixture is stirred for 5 minutes and is then washed with a saturated sodium bicarbonate solution, water, dilute hydrochloric acid, and then water. The dichloromethane solution is dried over anhydrous sodium sulfate. Upon removal of the drying agent and the solvent, crystalline material results which is isolated by filtration and washed with a small amount of cold methanol. The bisphenol A dicyanate product is recovered in a yield of 85.3 percent. The bisphenol A dicyanate has a gel time of about 5 hours.

EXAMPLE 4

Comparative Example, Not an Example of This Invention

A solution of bisphenol A (0.049 mole, 11.15 g) in a mixture of isopropyl alcohol (30 ml) and triethylamine (0.11 mole, 1.11 g) was added to a solution of commercial cyanogen chloride (0.11 mole) in dichloromethane (162 ml) at −10° C. over a period of about one hour. After the addition is complete, the reaction mixture is stirred for 5 minutes and then washed with a saturated sodium bicarbonate solution, water, dilute hydrochloric acid, and then water. The dichloromethane solution is dried over anhydrous sodium sulfate. Upon removal of the drying agent and the solvent, a crystalline material results which is isolated by filtration and washed with a small amount of cold methanol. The bisphenol A dicyanate isolated in 88 percent yield has a gel time of about 5 hours.

EXAMPLE 5

Comparative Example, Not An Example of This Invention

Chlorine (0.5 mole, 35.5 g) is introduced into 500 ml of dichloromethane which has been previously cooled to about −10° C. To this solution is added a solution of sodium cyanide (0.5 mole, 24.5 g) in 100 ml of water while maintaining the temperature of the solution at about −10° C. After the addition is complete, both the organic and the aqueous layers are colorless indicating the absence of unreacted chlorine. Gas chromatographic analysis of the organic layer shows a quantitative yield of cyanogen chloride. A solution of bisphenol A (0.15 mole, 34.2 g) in isopropyl alcohol (80 ml) and triethylamine (0.33 mole, 33.33 g) is added while maintaining the temperature of the reaction mixture at about −10° C. After the addition is complete, the reaction mixture is stirred for 5 minutes, and is then washed with a saturated sodium bicarbonate solution, water, dilute hydrochloric acid, and then water. The dichloromethane solution is then dried over anhydrous sodium sulfate. Upon removal of the drying agent and the solvent, a crystalline material results which is isolated by filtration and washed with a small amount of cold methanol. The bisphenol A dicyanate is recovered in a 45.5 percent yield, and the gel time of the bisphenol A dicyanate recovered is 2.5 hours.

This example demonstrates that the failure to remove the aqueous layer results in a lower yield of the desired product and a lower stability of the product, as evidenced by the significantly lower gel time of the product.

EXAMPLE 6

Comparative Example, Not an Example of the Invention

Example 4 is repeated, bisphenol A dicyanate is recovered in a 56.7 percent yield, the bisphenol A dicyanate has a gel time of 2.5 hours.

EXAMPLE 7

Comparative Example, Not an Example of this Invention

Chlorine (0.5 mole, 35.5 g) is introduced into 500 ml of dichloromethane previously cooled to about −10° C. To this solution is added a solution of sodium cyanide (0.5 mole, 24.5 g) in 200 ml of water while maintaining the temperature of the solution at about −10° C. After the addition is complete, both the organic and aqueous layers are colorless indicating the absence of unreacted chlorine. To the reaction solution is added a solution of bisphenol A (0.2 mole, 45.6 g) in isopropyl alcohol (100 ml) and triethylamine (0.44 mole, 44.44 g) while maintaining the temperature of the reaction mixture at about −10° C. After the addition is complete, the reaction mixture is stirred for 5 minutes and then washed with a saturated sodium bicarbonate solution, water, dilute hydrochloric acid solution, and then water. The dichloromethane solution is dried over anhydrous sodium sulfate. Upon removal of the drying agent and the solvent, a honey colored oil from which no desired product could be isolated is recovered.

EXAMPLE 8

Comparative Example, Not an Example of This Invention

Chlorine (0.5 mole, 35.5 g) is introduced into 500 ml of dichloromethane previously cooled to about −10° C. To this solution is added a solution of sodium cyanide (0.5 mole, 24.5 g) in 100 ml of water while maintaining the temperature of the solution at −10° C. A solution of bisphenol A (0.1 mole) in isopropyl alcohol (70 ml) and 0.22 mole of triethylamine is added while maintaining the temperature of the reaction mixture at about −10° C. After the addition is complete, the reaction mixture is stirred for 5 minutes and is then washed with a saturated solution of bicarbonate solution, water, dilute hydrochloric acid, and then water. The dichloromethane solution is then dried over anhydrous sodium sulfate. Upon removal of the drying agent and the solvent, a crystalline material results which is isolated by filtration and washed with a small amount of cold methanol. The bisphenol A dicyanate is isolated in a 23.8 percent yield with a gel time of 35 minutes.

EXAMPLE 9

A polyphenol is prepared by the acid catalyzed condensation of dicyclopentadiene with phenol. The polyphenol prepared corresponds to the following formula:

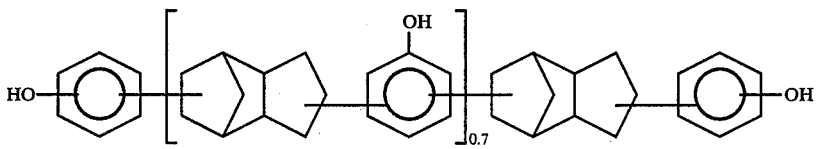

A solution of cyanogen chloride (0.175 mole) in dichloromethane is prepared in the manner described in Example 1. The organic layer is removed and transferred to another reactor, with care being taken to exclude the aqueous layer. To the organic reaction mixture is added a solution of the above described polyphenol (0.15 equivalent, 25.76 g) in dichloromethane (100 ml). Then triethylamine (0.153 mole, 15.45 g) is added while maintaining the reaction temperature at −10° C. After the addition is complete, the reaction mixture is stirred for 5 minutes and is then washed with a saturated sodium bicarbonate solution, water, dilute hydrochloric acid, and then water. The dichloromethane solution is dried over anhydrous sodium sulfate. Upon removal of the drying agent and the solvent, a polycyanate product is recovered which has a gel time of about 3 hours.

EXAMPLE 10

Following the procedure of Example 9, 1 mole of cyanogen chloride is prepared, and thereafter reacted with the polyphenol described in Example 9 (0.8 equivalent) in the presence of triethylamine (0.82 mole). The polycyanate recovered demonstrates a gel time of 3.5 hours.

EXAMPLE 11

Comparative Example, Not an Example of this Invention

A solution of cyanogen chloride (0.175 mole) in dichloromethane is prepared. The water layer is not removed in this example. To the reaction mixture is added a solution of the polyphenol described in Example 9 (0.15 equivalent, 25.76 g) in dichloromethane (100 ml). Then triethylamine (0.153 mole, 15.45 g) is added while maintaining the reaction mixture at −10° C. After the addition is complete, the reaction mixture is stirred for 5 minutes and is then washed with a saturated sodium bicarbonate solution, water, dilute hydrochloric acid, then water. The dichloromethane is dried over anhydrous sodium sulfate. Upon removal of the drying agent and the solvent, a heavy syrup which exhibited strong IR absorptions at 2,250 and 2,280 cm$^{-1}$ which are characteristic of cyanate groups, is recovered. The gel time of this material is 15 minutes.

What is claimed is:

1. A process for the preparation of an aromatic cyanate which comprises
    (a) preparing in situ a cyanogen chloride by contacting a solution of chlorine in a chlorinated hydrocarbon with an aqueous solution of an alkali metal cyanide at a temperature of 0° C. or below under conditions such that a cyanogen chloride is prepared;
    (b) physically separating the chlorinated hydrocarbon in which the cyanogen chloride is dissolved from the aqueous layer in which an alkali metal chloride salt is dissolved; and
    (c) contacting the cyanogen chloride dissolved in the chlorinated hydrocarbon with an aromatic phenol dissolved in a chlorinated hydrocarbon, a secondary alcohol or a tertiary alcohol, in the presence of a tertiary amine at a temperature of about 0° C. or less under conditions such that a aromatic cyanate is prepared.

2. The process of claim 1 wherein the aromatic cyanate corresponds to the formula Ar—(OCN)$_n$ and the aromatic phenol corresponds to the formula Ar—(OH)$_n$ wherein Ar is an aromatic radical and n is an integer of between 1 and 5, inclusive.

3. The process of claim 2 wherein the aromatic cyanate corresponds to the formula

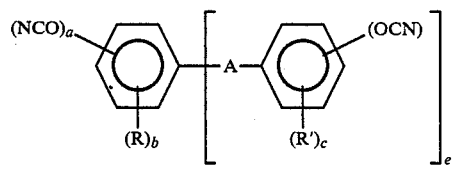

and the aromatic phenol corresponds to the formula

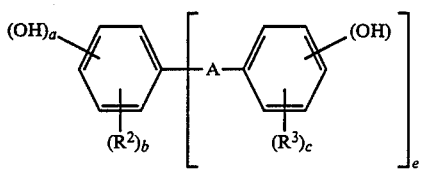

wherein
each R and $R^2$ is the same or different and represents hydrogen, halogen, straight and branched $C_1$-$C_{20}$ alkyl, phenyl, alkoxy radicals having from 1 to 4 carbon atoms, alkoxy carbonyl radicals having from 1 to 4 carbon atoms in the alkyl group or two adjacent radicals R or $R^2$ on the same nucleus may together form a carbocyclic 5- or 6-membered ring, two adjacent radicals R or $R^2$ may, together with a hetero atom (O, S, N), form a 5- or 6-membered heterocyclic ring;

R' has the same meaning as R or represents the group:

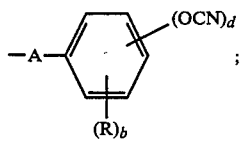

$R^3$ has the same meaning as $R^2$ or represents the group

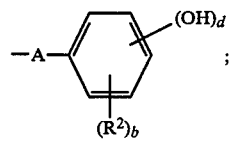

A represents a direct bond, a $C_1$-$C_{20}$ alkylene group optionally substituted by $C_1$-$C_4$ alkyl or phenyl, a cycloaliphatic or aromatic 5- or 6-membered ring optionally interrupted by oxygen, a polycyclic aliphatic group, a sulfonyl group (—$SO_2$—), a carbonyl dioxide group,

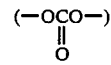

or a carbonyl group;
a represents a number of from 1 to 5 when $e \geq 1$, and a number of from 2 to 5 when $e=0$;
b represent 5-a when $e \geq 1$ and 6-(a+d) when $e=0$;
c represents 5-d;
d represents a number of from 0 to 5; and
e represents 0, 1, 2 or 3, with a proviso that the sum of a and d is always a number from 2 to 5.

4. The process of claim 3 wherein the temperature in step (a) is below about $-15°$ C.

5. The process of claim 4 wherein the temperature of step (c) is below about $-15°$ C.

6. The process of claim 5 wherein the mole ratio of alkali metal cyanide to chlorine in step (a) is between about 1.15:1 and 1.0:1.0.

7. The process of claim 6 wherein the mole ratio of cyanogen chloride to aromatic phenol is between 1.0:1.0 and 2.0:1.0.

8. The process of claim 7 wherein the mole ratio is between 1.10:1.0 and 2.0:1.0.

9. The process of claim 8 which further includes recovery of the aromatic cyanate from the reaction mixture in step (c) by
 (i) contacting the reaction mixture with a dilute aqueous solution of base;
 (ii) contacting the reaction mixture with water;
 (iii) contacting the reaction mixture with a dilute aqueous acid solution;
 (iv) contacting the reaction mixture with water;
 (v) drying the reaction solution to remove the water; and
 (vi) removing the organic solvent.

* * * * *